United States Patent
Gole et al.

(10) Patent No.: US 6,673,644 B2
(45) Date of Patent: Jan. 6, 2004

(54) POROUS GAS SENSORS AND METHOD OF PREPARATION THEREOF

(75) Inventors: James L. Gole, Atlanta, GA (US); Lenward T. Seals, Atlanta, GA (US); Peter J. Hesketh, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 10/268,860

(22) Filed: Oct. 10, 2002

(65) Prior Publication Data

US 2003/0139003 A1 Jul. 24, 2003

Related U.S. Application Data

(63) Continuation-in-part of application No. 09/820,412, filed on Mar. 29, 2001, now Pat. No. 6,589,883.
(60) Provisional application No. 60/328,583, filed on Oct. 10, 2001.

(51) Int. Cl.[7] .................................. H01L 21/00
(52) U.S. Cl. .................. 438/49; 438/48; 257/252; 257/253; 257/414; 73/23.22; 73/31.06
(58) Field of Search ................ 438/49, 48, 753; 257/252, 253, 414; 73/23.22, 31.06

(56) References Cited

U.S. PATENT DOCUMENTS

| | | | | |
|---|---|---|---|---|
| 4,969,025 A | * | 11/1990 | Yamamoto et al. | 357/30 |
| 5,394,735 A | * | 3/1995 | Fang et al. | 73/31.06 |
| 6,064,066 A | * | 5/2000 | Bevan et al. | 250/345 |
| 6,101,865 A | * | 8/2000 | Meixner et al. | 73/23.32 |
| 6,277,712 B1 | * | 8/2001 | Kang et al. | 438/471 |
| 6,444,487 B1 | * | 9/2002 | Boggs et al. | 438/48 |
| 2001/0046785 A1 | * | 11/2001 | Gole et al. | 438/753 |

OTHER PUBLICATIONS

James L. Gole, Lenward T. Seals, and Peter T. Lillehei; Patterened Metallization of Porous Silicon from Electroless Solution for Direct Electrical Contact; Journal of the Electrochemical Society; 2000; pp. 3785–3789.

Lenward Seals, James L. Gole, Laam Angela Tse and Peter J. Hesketh; Rapid, Reversible, Sensitive Porous Silicon Gas Sensor; Journal of Applied Physics; Feb. 15, 2002; pp. 2519–2523.

* cited by examiner

*Primary Examiner*—Alexander Ghyka
(74) *Attorney, Agent, or Firm*—Thomas, Kayden, Horstemeyer & Risley, LLP

(57) ABSTRACT

A sensor is disclosed. A representative sensor includes a silicon substrate having a porous silicon region. A portion of the porous silicon region has a front contact is disposed thereon. The contact resistance between the porous silicon region and the front contact is between about 10 ohms and 100 ohms.

17 Claims, 3 Drawing Sheets

POROUS GAS SENSORS AND METHOD OF PREPARATION THEREOF

CROSS-REFERENCE TO RELATED APPLICATION

This application is a continuation-in-part application, which claims priority to copending U.S. Utility Application entitled, "Enhancement, Stabilization and Metallization of Porous silicon," having Ser. No. 09/820,412, filed Mar. 29, 2001, now U.S. Pat. No. 6,589,883 which claims priority to copending U.S. Provisional Application entitled, "Novel Sensitive Porous Silicon Gas Sensor," filed on Oct. 10, 2001, and assigned Serial No. 60/328,583, both of which are entirely incorporated herein by reference.

TECHNICAL FIELD

The present invention is generally related to porous silicon substrates and, more particularly, is related to porous silicon sensors and methods of preparation thereof.

BACKGROUND OF THE INVENTION

High surface area porous silicon (PS) substrates formed in wafer scale through electrochemical (EC) etching fall into two groups. PS substrates fabricated from aqueous electrolytes consist of highly branched nonporous substrates while PS substrates fabricated from a aqueous electrolyte are comprised of open and accessible macroporous substrates with deep, wide, well-ordered channels.

High-surface area silicon substrates formed in wafer scale through etching display a visible photoluminescence (PL) upon excitation with a variety of visible and ultraviolet light sources. This room-temperature luminescence has attracted considerable attention primarily because of its potential use in the development of silicon-based optoelectronics, displays, and sensors.

Although the PL is thought to emanate from regions near the PS substrate surface, the origin of the PL is the source of some controversy as the efficiency and wavelength range of the emitted light can be affected by the physical and electronic properties of the surface, the nature of the etching solution, and the nature of the environment into which the etched sample is placed. Given this range of parameters, it is surprising that, with few exceptions, PL spectra are reported for PS substrates formed in dilute aqueous HF solutions, that have already been dried in air or more inert environments following etch and rinse treatments. These ex situ samples, while providing spectral information, do not indicate the evolution of the PS substrates, and thus, they do not indicate means by which it might be modified and enhanced during or following the etch treatment.

An existing problem in fabricating PS devices rests with establishing electrical contact to the PS substrates. Another problem with PS includes the relatively long excited-state lifetime associated with the PS substrate PL. A further problem includes the relatively low PL quantum yield and the instability of the PL from PS substrates. An additional problem includes that small, sensitive, and selective sensors are not readily available at cost effective prices.

Thus, a heretofore unaddressed need exists in the industry to address the aforementioned deficiencies and inadequacies.

SUMMARY OF THE INVENTION

An embodiment of the present invention provides for a sensor. A representative sensor includes a silicon substrate having a porous silicon region. A portion of the porous silicon region has a front contact disposed thereon. The contact resistance between the porous silicon region and the front contact is between about 10 ohms and 100 ohms.

Another embodiment provides for a method of fabricating a sensor. The fabrication includes: providing a silicon substrate; converting a first region of the silicon substrate into a porous silicon region; forming a first front contact onto a first portion of the porous silicon region; and forming a second front contact onto a second portion of the porous silicon region, wherein a third portion of the porous silicon region is between the first front contact and the second front contact.

Other systems, methods, features, and advantages of the present invention will be or become apparent to one with skill in the art upon examination of the following detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 1A is a top view of a representative embodiment of the porous silicon sensor of the present invention, while

FIG. 2A is a top view of a representative embodiment of another porous silicon sensor of the present invention, while

DETAILED DESCRIPTION OF THE PREFERRED EMBODIMENT

Figure 1A:
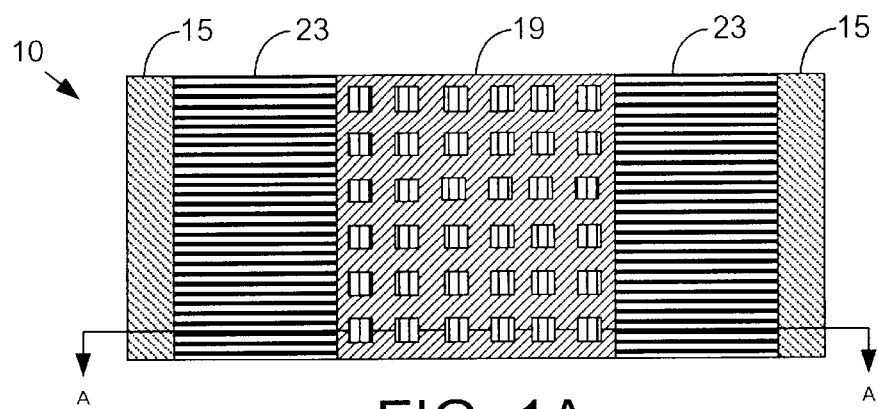

1. Stabilization and Enhancement of Porous Silicon

One of a number of embodiments of the present invention includes the treatment of PS substrates generated in an aqueous and nonaqueous etch with an HCl(H$_2$O) solution, which results in the stabilization and enhancement of the in situ PL of the PS substrates. More specifically, in an exemplary embodiment, in a post-etch treatment method, an HCl(H$_2$O) solution can be used to enhance and stabilize the PL (in situ) from a PS substrate. In addition, in an other exemplary embodiment, a method of treating the PS substrate with HCl(H$_2$O) followed by an alcohol solution (e.g. methanol or ethanol) further enhances and stabilizes the PL (in situ and ex situ) of the substrate. A non-limiting illustrative example includes PS substrates that are treated in an aqueous hydrochloric acid and water (HCl/H$_2$O) solution and display a strongly enhanced in-situ luminescence;

however, the PL decays rapidly in an ex-situ environment without treatment in alcohol, preferably a high purity alcohol such as methanol. An exemplary embodiment includes treating the PS with methanol (MeOH). Further, PS substrates treated in an HCl(H$_2$O)/alcohol solution (of at least 0.2 molar (M)) maintain their enhancement for extended periods of time. The PS substrate may be stabilized and enhanced by the presence of a chloride ion (Cl$^-$). The treatment appears to be independent of the method of preparing the PS substrate, implying that the chloride salt treatment largely stabilizes the surface states of the photoluminescent PS substrate. This stabilization may be demonstrated by various techniques including, but not limited to the following: scanning electron micrographs (SEM), which show the profound change which accompanies the HCl treatment of the PS surface; Energy Dispersive Spectroscopy (EDS) which, reveals chloride incorporation into the PS surface at strongly photoluminescent regions; and Raman scattering, which demonstrates that the PL is correlated with the creation of amorphous structural regions. All of these testing methods indicate the manner in which the chloride salt stabilizes the PS substrate.

2. Enhancement of the PS Photoluminescence Using Dyes

Another exemplary embodiment of the present invention includes treating PS substrates with a dye (e.g., 3,3'-diethyloxadicarbocyanine iodide (DODCI) and Rhodamine 700). In general, the dye should have negligible absorption at the wavelengths of maximum absorption for the PS substrate. After a period of aging in darkness these dye-treated PS substrates can be pumped at about 337.1 nanometers (nm) (nitrogen laser) near the maximum in the PS absorption spectrum (far from the major absorption regions of the impregnating dye). Time-dependent PL histograms indicate that the resulting PL emission rate is enhanced. The enhancement in the PL emission rate may be attributed to an interaction between the surface-bound fluorophors, which characterize PS substrates and the dye. This interaction results in the creation of a distribution of PS-dye complexes, which enhance the nominal PL emission rate from the untreated PS surface. In a preferred embodiment, the DODCI treated samples display PL that exceeds that of nominally prepared PS by a factor of five or more.

3. Metallization of PS

A further exemplary embodiment of the present invention includes the metallization of a PS substrate. One of the existing challenges in fabricating PS devices rests with establishing electrical contact to the PS substrate. In an exemplary embodiment, PS substrates are capable of being metallized in a controlled manner using electroless metal-coating solutions and inducing the metal to plate onto the PS substrate in regions which are PL. An exemplary embodiment includes using an electroless metal solution, which can be introduced to the PS substrate after treating the PS substrate with a hydrazine solution so that subsequently the metal can be deposited onto the PS substrate in a controlled manner. The metal-containing solution includes, but is not limited to, any one, or all, or combination of copper, silver, gold, and other metals that are commonly deposited using electroless techniques. This method is capable of using the "long-lived" PS substrate PL to enhance reduction at the PS substrate surface. This may be accomplished by creating excited fluorophors on the PS surface to enhance interaction and reduction at the PS substrate surface. Using this method enables metals to readily deposit onto the PS substrate within PS micropores and nanopores. Further, under controlled conditions the metallization only occurs where the PS surface is illuminated with light from a light source. (e.g. Xenon (Xe) arc lamp, Helium-Neon (HeNe) laser, or other appropriate light source). Furthermore, the thickness of the metallization deposit is proportional to the time and intensity of exposure of the PS surface to the light source.

In conventional electroless metal plating, the surface is usually first coated with palladium (Pd) metal to catalyze the deposition process. For purposes of this disclosure, the addition of a catalyst to the metal plating process is considered to be operating under catalytic conditions. However, embodiments of the present invention do not require an additional catalyst, which, for purposes of this disclosure, means that the method is performed under "non-catalytic conditions." Indeed, in the method of the present invention, the illuminated PS surface itself is catalyzing the deposition. Further, localized heating is not promoting the deposition; rather the metal deposition occurs when the PS substrate is illuminated at wavelengths less than about 750 nm, consistent with its bandgap.

A further exemplary embodiment of the present invention includes the metallization of a PS substrate to produce a low electrical resistance metallized PS substrate that has a resistance from about 20 ohms to about 1000 ohms. Another embodiment includes metallized PS substrates with resistances between about 20 ohms and about 100 ohms. Still a further embodiment includes metallizated PS substrates with resistances between about 20 ohms and about 60 ohms.

4. Porous Silicon Sensor

A further exemplary embodiment of the present invention includes a porous silicon (PS) sensor. The PS sensor includes a silicon substrate, a PS layer on a portion of the silicon substrate, and a front contact disposed onto a portion of the PS region. The PS region can include a nanoporous or a macroporous and nanoporous hybrid framework. In the preferred embodiment, the front contact can be disposed within the macroporous and nanoporous hybrid framework. The front contact can include one or more front contact portions made of metals such as, for example, copper, silver, and gold.

The PS sensor can be used to detect gases or liquids. In particular, PS gas sensors, in accordance with the present invention, have a rapid and reversible response to analyte gases at room temperature. The PS sensor has a contact resistance between the front contact and the PS between about 10 and 100 ohms, 20 to 100 ohms, and preferably about 20 and 60 ohms. In addition, the PS sensor has a resistivity between about 0.01 ohms/cm$^2$ to 1 ohms/cm$^2$, and preferably about 0.1 ohms/cm$^2$ to 1 ohms/cm$^2$. Further, the PS sensor operates at a bias voltage of between about 1 and 20 millivolts, and preferably about 1 to 10 millivolts. The PS sensors have a sensitivity of at least as low as 10 parts per million (ppm).

1. Stabilization and Enhancement of Porous Silicon

HCl(H$_2$O)/Alcohol PL Enhancement of Porous Silicon Substrates

As discussed above, an exemplary embodiment of the present invention includes a method and system of treating PS substrates with an HCl/(H$_2$O) solution to enhance and stabilize the PL of the PS substrates. PS substrates treated in an HCl/(H$_2$O) solution display a strongly enhanced in situ PL. PS substrates treated in an HCl/(H$_2$O) alcohol solution (e.g. at least 0.2 M display enhanced in situ and ex situ PL and can maintain enhancement for time periods on the order of years. Another exemplary embodiment includes treating the porous silicon substrates with an HCl/(H$_2$O) solution (e.g. at least 0.2 M) then subsequently treating the PS substrates with an alcohol. This embodiment also enhances and stabilizes the in situ and ex situ PL of the PS substrate.

More specifically, the post-etch method of enhancing and stabilizing the PL of a PS substrate includes treating the PS substrate with an $HCl/(H_2O)$ solution. The PS substrate includes, but is not limited to a microporous framework upon which is superimposed a nanoporous layer. The $HCl/(H_2O)$ solution is at least 0.2 M. In one exemplary embodiment, the $HCl/(H_2O)$ solution includes an alcohol. Alcohols that can be used include, but are not limited to, ethanol, methanol, other appropriate alcohols for treating PS substrates, and combinations thereof. In another exemplary embodiment, the PS substrate is treated with the $HCl/(H_2O)$ solution, then subsequently treated with an alcohol (e.g., ethanol, methanol, etc.) This method of treatment enhances the in situ and enhances and stabilizes the ex situ PL.

Chloride-ion stabilization appears independent of the method of preparing the PS substrates, implying that the chloride salt treatment largely stabilizes the surface constituency of the photoluminescent PS substrate. This can be demonstrated by scanning electron micrographs, which show the change that accompanies the HCl treatment of the PS substrate surface. Further, energy dispersive spectroscopy reveals chloride incorporation into the PS surface at strongly PL regions. Furthermore, Raman scattering demonstrates that the PS substrate PL enhancement is correlated with the creation of amorphous structural regions. In conjunction with detailed quantum-chemical modeling, time-dependent histograms obtained for the HCl-treated systems indicate that the resulting PL, initiated through the optional pumping of the HCl-modified surface, displays the manifestation of a significant surface interaction. This interaction might result in the formation of both chlorosilanones and chlorsilylenes. In addition, the hydrogen cation ($H^+$) may play a role in the stabilization of the silanol-based features of the PS substrate surface both as a contribution to the flourophor formation and by decreasing the hydroxyl ($OH^-$) concentration in solution.

EXAMPLE 1

Preparation of PS

The following is a non-limiting illustrative example of an embodiment of the present invention that is described in more detail in Gole, et al., Phys. Rev. B, 61, 5615 (2000); Gole, et al., J. Phys. Chem. 101, 8864 (1997); Gole, et al. Phys. Rev. B, 62, 1878 (2000), which all are herein incorporated by reference. This example is not intended to limit the scope of any embodiment of the present invention, but rather is intended to provide specific experimental conditions and results. Therefore, one skilled in the art would understand that many experimental conditions can be modified, but it is intended that these modifications are within the scope of the various embodiments of this invention.

a. PS Preparation

Single crystal <100> boron doped silicon wafers with resistivities of about 50–100 $ohm/cm^2$ were used in the current study. Both highly branched nanoporous and hybrid nanoporous-covered microporous PS substrate samples were fabricated in an electrochemical cell constructed from high-density polyethylene. The working electrode was attached to the back of a p-type silicon wafer <100> (aluminum (Al) coated) and the counter electrode corresponded to a platinum (Pt) foil placed in solution. The cell was sealed to the front of the wafer, using a clamp, as about a 1 centimeter squared ($cm^2$) section of the wafer made contact with the solution. A magnetic stir-bar was used to prevent the build-up of hydrogen at the surface of the silicon. The electrochemical etching current was supplied by an Potentiostat/Galvanostat. The nanoporous samples were etched in an aqueous 25% hydrofluoric acid (HF) in methanol solution while the hybrid nanoporous-covered microporous samples were etched in a solution of 1 M $H_2O$, 1M HF, and 0.1M tetrabutylammonium perchlorate (TBAP), all in acetonitrile. The nanoporous etched samples were etched at a current density ranging from about 2 to 30 miliamp per centimeter squared ($mA/cm^2$) and preferably about 8 $mA/cm^2$ for about 50 to 75 minutes while the hybrid samples were etched with a current density of about 8 $mA/cm^2$ for between 50 and 75 min. Using this latter procedure, pores approximately 1 to 2 $\mu m$ wide by about 10 $\mu m$ deep were formed, and well covered by a coating of nanoporous silicon.

b. PS Preparation

Single-crystal <100>, boron-doped silicon wafers (substrate) of resistivity ranging from about 1 to about 50 $ohm/cm^2$ were also etched in an alternative aqueous HF solution. For several of the experiments (about 20% concentration of HF in methanol), a 300-nm thin film of aluminum was sputtered onto the backside of the wafers. Electrical connections were made to the wafers by connecting a wire to the thin film of aluminum using conductive paint. The wire and aluminum film were then covered with a layer of black wax, leaving only the front surface of the silicon exposed to the etching solution. Both the wired silicon-wafer as one electrode and a platinum wire as a counter-electrode may be connected through a Teflon™ cap, which was tightly fitted to a cuvette containing the etch solution. Ohmic contacts were made to the wafer by connecting a wire to the thin film of aluminum using conductive paint. Etching currents ranged from about 2 to 30 $mA/cm^2$, but the samples considered here were usually etched at 8 $mA/cm^2$ for 10 minutes.

These aqueous HF-etching procedures are capable of leading to the formation of a "nanoporous" surface on the silicon wafer. However, in order to obtain a thicker nanoporous coating and increase the sampling volume, Si <100> samples were treated in a 25% HF in methanol solution at a current density of about 14 $mA/cm^2$ for a period of about 30 min. In all cases, the prepared aqueous samples were either treated directly in solution or washed in spectral quality methanol and dried in air. They were then subsequently transferred to a crucible containing either methanol or the post-etch chloride solution of interest.

Samples prepared in about 20% HF/MeOH aqueous etching solution, once rinsed in a combination of doubly deionized water and methanol or ethanol and allowed to dry, yield a significant ex situ photoluminescence. If a cleaned sample is immediately placed in double deionized water, a gradual rise in the in situ PL intensity at 620 nm can be observed. Similarly, if such a cleaned sample is placed in an ultra high purity low molecular weight alcohol (e.g. methanol and ethanol) solution, the in situ PL will slowly increase and gradually diminish on the time scale of several hours. However, it is to be noted that this behavior is in sharp contrast to the effect of the alcohols in combination with HF: this combination rapidly quenches the PL within several minutes.

c. PL Stabilization Using HCl Treatment

The post-etch treatment of the PS substrates with an aqueous HCl solution and the enhancement and stabilization is now discussed. A PS sample prepared by aqueous etch is first etched in a methanol/20% HF [6 mol/l HF in MeOH (aq)] solution for 10 min., washed with methanol, dried in air, and then placed first in a solution of doubly deionized water and then dilute 6M HCl. The intensity of the PL, excited by a nitrogen ($N_2$) laser, increases somewhat upon removal from the HF etch solution and again increases gradually as the sample is placed in water. However, upon adding HCl the orange-red PL intensity increases significantly and remains constant over the time period (up to about 3.5 h) in which the sample is present in the HCl solution. Within the time frame of these processes, the wavelength-dependent spectral profile of the PL emission spectrum appears to have been altered only slightly from the time it was removed from the HF etching solution and dried in air through the period in which the sample remained in the HCl solution. The introduction of a high concentration of HCl has stabilized the PS photoluminescence.

In contrast to the stabilizing effect that 6M hydrochloric acid has on the PS substrates surface, a 2.75M hydrogen iodide (HI) solution almost completely quenches the PL. The effect of a 4.5M hydrogen bromide (HBr) solution is intermediate. The effect of the HI solution can be attributed to the strong quenching of surface-bound flourophors resulting from the formation of $I_2$ and $I_3$ in an oxidizing acidic environment. A similar effect also occurs with bromine, albeit to a much lesser extent.

d. PL Stabilization Using NaCl Solution Treatment

Post-etch treatment of the PS substrate in a methanol-NaCl solution is now discussed. The pronounced stabilization of the PS substrate photoluminescence in the 6M HCl solution focuses on the effect that the chloride ion may have on the PL process. The introduction of an aqueous etched (20% HF/MeOH) PS substrate sample into a saturated NaCl/MeOH solution produces a clear saturating PL emission signal. This is manifest in two ways. In the absence of sodium chloride (NaCl), the 620-nm PL from the PS substrate placed in methanol solution slowly rises, eventually peaks, and then more gradually decreases in intensity. If NaCl is placed into this solution before the PL has reached its maximum intensity in methanol, the PL will slowly increase to a maximum then plateau. For the introduction of the PS substrate sample into a NaCl-saturated solution in methanol, this plateau is reached over a time scale of several hours (compared to about 30 min for a 6M HCl solution). Furthermore, the photon-count level at the maximum PL intensity appears to be considerably muted relative to the observed maximum for a PS substrate sample in methanol alone. In contrast, if the saturated NaCl solution is introduced to the methanol solution after the PL photon-count level has peaked in the methanol solution, the PL is found to plateau at an intensity corresponding closely to that at the time of the NaCl introduction.

e. Treatment Using Tetrabutylammonium Chloride

Post-etch treatment of PS substrate samples in tetrabutylammonium chloride (TBAC) solution is now discussed. The results observed when placing a prepared PS substrate sample in 6M HCl and saturated NaCl solutions certainly call attention to the potential role of the chloride ion in stabilizing the PS substrate photoluminescence. In order to study the effect of varying chloride-ion concentrations on the PS substrate luminescence, both tetrabutylammonium perchloride (TBAC) and HCl solutions are studied.

The PS substrates PL at 620 nm is monitored after a sample, etched in a 20% HF/MeOH solution, is washed in methanol, dried in air, and then placed in a tetrabutylammonium chloride (TBAC) in methanol solution. The TBAC concentrations used include 0.1M, 0.2M, 0.3M, 0.4M and 1.0M. These experiments can be used to compare directly to the NaCl/MeOH saturated solution results. The 0.1M TBAC solution leads to a PL intensity, which peaks at about 4300 counts, seventy five minutes into the bath cycle, and then monotonically decreases to about 1000 counts within 5 hours. The source of the PS luminescence is temporarily enhanced, but it is not being stabilized at longer time scales. When the chloride concentration is raised to 0.2M, the photon-count level increases moderately as the PL intensity peaks at about 4800 counts, now 150 min. into the bath cycle. The signal again monotonically decreases to about 1000 counts within 5 hours. This trend continues for the 0.3M solution as the PL intensity peaks at about 6500 counts, 240 min into the run; however, despite a significant peak photon count, an eventual drop-off of the PL signal is observed. The 0.4M chloride-ion solution again demonstrates an increased photon-count level (peak about 12000 counts). There is also a notable decrease in the rate of PL decay. This trend appears to reverse for the 1M concentrated $Cl^-$ solution. Although the PS luminescence peaks on a shorter time scale, the PL peak level has dropped to about 6000 counts and also decays at a much more rapid rate, clearly paralleling that for the 0.1M and 0.2M solutions. Thus, for the tetrabutylammonium counterion ($TBA^+$), evidence is produced for a peak effective chloride-ion concentration but no evidence is produced for an extended stabilization of the PL signal with time.

f. HCl Concentration Effect on PL

In situ stabilization in HCl solutions of varying concentrations is now discussed. The results obtained in saturated NaCl and TBAC solutions emphasize the remarkable PL stabilization that is inherent to a PS sample bathed by a 6M HCl solution. Next, a comparison of various concentrations of HCl is conducted. The concentrations include 0.1M, 0.2M, 0.3M, 1M, 2M, and 3M. For a 3M HCl solution in either water or methanol, the photon count rate is comparable to that for the 6M HCl solution. The count rate is still rising after 6.5 h in dilute HCl, whereas it levels off at about 20000 counts in the 6M HCl/($H_2O$) MeOH solution after approximately 2 h. Both bath solutions demonstrate a profound stabilizing and enhancing effect on the PS emission intensity.

As the HCl molarity decreases, there are clear subtle changes in the in situ PL. For the 2M and 1M dilute HCl/($H_2O$) solutions, the count rate is again comparable to that for the higher molarities and still rising after 6 h; however, the count rate in the 2M HCl/MeOH solution has already dropped to about 14000 (although appearing reasonably stabilized) and shows an even sharper decline for the 1M solution where a maximum intensity of about 5000 counts occurs about 2 h into the time scan and a precipitous decrease to barely 3000 counts is observed at 6 h.

The HCl-water system displays a remarkable in situ enhancement and stabilization. With further dilution to 0.3M, one finds a comparable but possibly a slightly increased enhancement of the PL intensity is observed, which is still rising to about 25,000 counts after 6 h of PS substrate sample exposure to the HCl solution. At 0.2M, the HCl solution again displays a comparable stabilization that appears to plateau at about 22000 counts. However, at 0.1M, the HCl solution induces a much smaller enhancement of the PL signal from a sample photoluminescing in doubly deionized water. Furthermore, the stabilization of the signal is marginal as shown by a peaking at about 2625 counts approximately 4 h into the run. The threshold for stabilization and enhancement thus appears quite dramatic.

The results shown for HCl suggest the importance of the $H^+$ counterion generated from the strong acid HCl as well as the chloride ion. The $H^+$-ion concentration may play a role in stabilizing silanol-based features on the PS substrate surface both as a contributor to flurophor formation and by decreasing the [$OH^-$] concentration in solution. This is supported because the introduction of NaOH into this bath solution completely quenches the PL as it significantly increases the hydroxyl-ion concentration.

Ex situ PL from HCl-treated PS substrates is now discussed. The samples that have been treated in HCl ($H_2O$)/MeOH and HCl/$H_2O$ solutions exhibit distinctly different ex situ behavior. The following demonstrates the different behavior. The growth of the in situ PL emission in a 1M HCl($H_2O$)/MeOH solution peaks at about 12500 counts. Upon removal from the HCl($H_2O$)/MeOH bath, the ex situ PL emission intensity continues to maintain itself for periods exceeding several months. A similar treatment of the PS substrate surface in 3M HCl($H_2O$)/MeOH also produces a highly photoluminescent ex situ sample with a considerably higher long-term photoluminescent emission intensity peaking at about 18000–20000 counts (about 620 nm). In sharp contrast, if a PS substrate sample treated in an HCl/$H_2O$ solution and characterized by a PL emission intensity close to 20000 counts is removed from the solution and dried in air, the PL emission intensity drops to about 4000 counts at 620 nm within 24 h even decreasing precipitously during the laser pumping and PL measurement period to about 3000 counts. Another comparison shows long-term PL stability, for a 1M HCl/$H_2O$-tested sample that is immediately placed in ultra high purity methanol. The PL scans display not only a long-term stability but also a peak intensity considerably red-shifted (~500 Å). The ex situ PL signal from an HCl/$H_2O$ solution-treated sample is almost completely extinguished within only a few days. However, if the PS substrate sample is rinsed in ultra high purity methanol after an in situ HCl/$H_2O$ treatment and allowed to remain in a methanol solution for two to three days, the PL intensity can significantly be maintained, ex situ, indefinitely.

2. Dye Enhanced PL of PS Substrates

Room temperature PL of PS substrates has attracted considerable attention primarily because of its potential use in the development of silicon based optoelectronics, displays, and sensors. However, the relatively long excited state lifetime associated with this PL, which appears to be of the order of tens to hundreds of microseconds, is problematic for some of these applications. The efficiency and wavelength range of the emitted light can be affected by the physical and electronic structure of the surface, the nature of the etching solution, and the nature of the environment into which the etched sample is placed.

These outlined results suggest the possibility that several common fluorescent dyes, whose radiative lifetimes are of the order of nanoseconds, might be made to interact with the PS substrate surface so as to considerably improve the observed PL rate. Strong physisorption or chemisorption of certain of these fluorescent dyes with the fluorescent emitter on the PS substrate surface through complexation enhance the quantum yield and modify the lifetime of the fluorescent events associated with the PS substrate.

More specifically, the post-etch enhancement of the PL from a PS substrate, which has a microporous framework on which is superimposed a nanoporous layer, includes treating the PS substrate with a dye. The dyes that can be used include, but are not limited to, 3,3-diethyloxadicarbacyamine iodide, Rhodamine dye compounds (e.g. Rhodamine 6G, Rhodamine 700), Fluorocein, dicyanomethylene (DCM) dye compounds (e.g. 4-dicyanomethylene-2-methyl-6-(p-dioctylaminostyryl)-4H-pyran, 4-dicyanomethylene-2-methyl-6-(p-dimethylaminostyryl)-4H-pyran, 4-dicyanomethylene-2-methyl-6-[2-(1-methyl-1,2,3,4-tetrahydroquinolin-6-yl)ethenyl]-4H-pyran), 4-dicyanomethylene-2-methyl-6-[2-(2,3,6,7-tetrahydro-1H, 5H-benzo[ij]quinolizin-8-yl)etheny]-4H-pyran), and other dyes that have negligible absorption at the wavelengths of maximum absorption for the PS substrate.

EXAMPLE 2

The following is a non-limiting illustrative example of an embodiment of the present invention and is described in more detail in Gole, et al., J. Phys, Chem. B, 103, 979 (1999), which is incorporated herein by reference. This example is not intended to limit the scope of any embodiment of the present invention, but rather is intended to provide specific experimental conditions and results. Therefore, one skilled in the art would understand that many experimental conditions can be modified, but it is intended that these modifications are within the scope of the embodiments of this invention.

As discussed in examples 1 and 2, single crystal <100> boron doped silicon wafers with resistivities of about 50–100 ohm-cm were used in the current study. Both highly branched nanoporous and hybrid nanoporous covered microporous PS substrate samples were fabricated in an electrochemical cell constructed from high-density polyethylene. The working electrode was attached to the back of a p-type silicon wafer <100> (aluminum coated) and the counter electrode corresponded to a platinum foil placed in solution. The cell was sealed to the front of the wafer, using a clamp, as about a 1 $cm^2$ section of the wafer made contact with the solution. A magnetic stir-bar was used to prevent the build-up of hydrogen at the surface of the silicon. The electrochemical etching current was supplied by an Potentiostat/Galvanostat. The nanoporous samples were etched in an aqueous 25% HF in methanol solution while the hybrid samples were etched in a solution of 1 M $H_2O$, 1M HF, and 0.1M tetrabutylammonium percholate (TBAP), all in acetonitrile. The aqueous etched samples were etched at a current density ranging from about 2 to 30 mA/$cm^2$, and preferably about 8 mA/$cm^2$, for about 50 to 75 minutes while the hybrid samples were etched with a current density of about 8 mA/$cm^2$ for between 50 and 75 min. Using this latter procedure, pores approximately 1 to 2 $\mu$m wide by about 10 $\mu$m deep were formed, and well covered by a coating of nanoporous silicon.

Further, as discussed in example 1, single-crystal <100>, boron-doped silicon wafers (substrate) of resistivity ranging from about 1 to about 50 ohm/$cm^2$ were also etched in an aqueous HF solution. For several of the experiments (about 20% concentration of HF in methanol), a 300-nm thin film of aluminum was sputtered onto the backside of the wafers. Electrical connections were made to the wafers by connecting a wire to the thin film of aluminum using conductive paint. The wire and aluminum film were then covered with a layer of black wax, leaving only the front surface of the silicon exposed to the etching solution. Both the wired silicon-wafer as one electrode and a platinum wire as a counter-electrode could be connected through a Teflon cap, which was tightly fitted to a cuvette containing the etch solution. Ohmic contacts were made to the wafer by connecting a wire to the thin film of aluminum using conductive paint. Etching currents ranged from about 2 to 30 mA/$cm^2$, but the samples considered here were usually etched at 8 mA/$cm^2$ for 10 minutes.

Prepared aqueous and hybrid samples were removed from the etching solution, washed in reagent grade methanol and treated with $10^{-3}$ molar (in doubly distilled $H_2O$) 3,3-diethyloxadicarbocyanine iodide (DODCI) or Rhodamine 700. The PS substrate samples were dipped for several seconds or soaked for periods extending to about 45 minutes.

Pore structure and PL emission from PS substrates for untreated PS substrate samples is now discussed. The PL emission from aqueous and hybrid etched samples observed over the period 1.5–100 µs after excitation (PLE) at 337.1 nm (t=0) suggests that the PL observed for the hybrid etched sample exceeds that for the aqueous etched sample and demonstrates a slight 10–15 nm red shift.

PS substrates are known in the art to display a "green" PL resulting from an intermediate precursor state in the earlier stages of the emission process. The temporal decay and spectral profile of the "green" PL and transformation to a final "orange-red" PL emission during and following PS formation suggest the coupling of these PL emitters to the PS surface. The manifestations of the green and orange-red emission features in spectra are virtually identical for the aqueous and hybrid etched samples. Observed spectrum histograms represent the first clear observation of the "green" luminescence feature in an air-aged sample and demonstrate the magnitude of its contribution to the overall spectrum. With time (1) the "green" and "orange-red" emission features merge into each other as the source of the green emitter undergoes oxidative transformation to the final "orange-red" emitter, and (2) the longer wavelength features contributing initially to the orange-red emission are seen to decay most rapidly leading to what appears to be the manifestation of a blue shift in this feature in the absence of etching.

After 5.5 µs, for the aqueous etched sample, and 9.5 µs for the hybrid etched sample, the observed spectral features change little with delay time and the emission signal over the gate width of the scan begins to decrease. The dominant characteristics of the 1.5–100 µs spectra develop over the time span of the histograms, and with longer time delays, the monitored emission, while maintaining an identical wavelength dependence, decreases precipitously in intensity. The data demonstrate a nearly parallel although slightly different development of the PL intensity for the aqueous and hybrid etches and an overall spectral distribution which is quite similar for these etched samples.

Dye-treated PS substrates are now discussed. Dyes, such as DODCI and Rhodamine 700, have been used because of their negligible absorbance in the 350±20 nm range, the approximate peak absorption range of the PS excitation spectrum. The absorption spectrum for DODCI demonstrates a minimal absorbance for λ=330–470 nm. Rhodamine 700 is also a reasonable candidate although this dye does display a small absorbence at λ<330 nm.

Here, the focus is to create an environment for the energy transfer pumping of the adsorbed dye and/or the mediation of the longer-lived fluorescence from the PS substrate due to PS-dye complexation. As the optical pumping of the PS substrate surface is known to access a long-lived excited state triplet exciton, this excited state can be an energy reservoir for subsequent energy (or electron) transfer between the PS substrate surface and the adsorbed dye. Such transfer might take place through the pumping of a dye molecule in close proximity to the PS substrate surface via a fast intermolecular electron transfer. Alternatively, the dye chemisorbed with the surface-active exciton could receive the exciton energy via fast intramolecular energy transfer along a short bonding chain. Finally, the presence of this much more efficient radiator could enhance the PS substrate emission rate simply through complexation with the PS fluorophors.

Samples exposed to DODCI or Rhodamine 700 dye, when pumped at 337.1 nm by a nitrogen laser, display an initial quenching of the PS substrate PL followed by an expected slow and continued increase in the PL emission rate upon aging in the dark, in air, for an extended period. The aging cycle eventually produces a PL signal which has been maximized and maintained for a period of several months.

After some period of aging, the DODCI treated sample is found to display a photoluminescence corrected for phototube and system response which exceeds the intensity of a nominally prepared PS substrate sample by a factor of five. Further, the distribution of fluorescence is notably broader with a peak response considerably red shifted (about 30–50 nm) from an aqueous etched untreated PS substrate sample. This is consistent with a PS-dye coupling. Note that, as opposed to high temperature annealing at temperatures between 100° C. and a very significant 600° C. for short periods to promote oxidation on the PS substrate surface, this embodiment shows a long-term aging process under conditions which promote the conversion of the surface and ensure a dye initiated modification without seriously modifying the interacting constituencies.

Simple immersion or prolonged soaking of the PS substrates in millimolar (mM) dye solutions is sufficient not only to position the dye in close proximity to the surface bound PS emission centers but also to promote its interaction. The most pronounced interaction is manifest for those samples treated in DODCI. The effects observed for both DODCI and Rhodamine 700 are greatest for those samples treated after aqueous etching.

A histogram with delays ranging from 0.5 to 61.5 µs (5 µs gate) for the DODCI treatment of an aqueous etched sample shows a convergence to a dominant feature peaking at about 650 nm. By comparison, a histogram of the PL for time delays of 0.5 to 11.5 µs (5 µs gate) demonstrates the evolution observed for an untreated aqueous etched sample. The DODCI treated sample is distinct, displaying initially both a "green" emission feature and an "orange-red-red" emission feature which at first appear to "bookend" the observed aqueous etch emission features. With increased delay time, the green emission feature red shifts and the red emission feature appears to split into two features, one of which blue shifts with increased delay time and a second peak which appears almost stationary in time. This gives the appearance of a triple peaked spectrum for time delays ranging from 7.5 to 23.5 µs. After a 27.5 µs delay, the shifting short wavelength and orange-red features have virtually merged into each other to form a dominant peak at about 640 nm which eventually red shifts by about 10 nm. The observed spectra after 27.5 µs suggest that the continued red shifting of the initially green emission feature somewhat dominates the observed time dependence. The peak spectral intensity observed in a given histogram remains virtually constant out to 33.5 µs.

The interaction of Rhodamine 700 with an aqueous etched PS substrate sample appears to be much less pronounced than that for DODCI. The shifting green and orange-red emission features have merged in the 7.5 µs delay scan to a dominant spectral peak at 640 nm which red shifts to 650 nm by 21.5 µs. Further, the drop off in spectral intensity occurs considerably more rapidly.

In another histogram obtained for a DODCI treated hybrid etched sample, initially soaked for 45 minutes in a $10^{-3}$ M dye solution, the dye has a clear affect on the hybrid etched sample although not as pronounced as that on the aqueous etched sample. Further, the extended period of exposure to the dye is required as a hybrid sample simply dipped in DODCI is found to rapidly converge to a strongly dominant 630–640 nm feature indicative of the untreated hybrid etch. In another histogram, the PL for the DODCI treated sample is compared to the evolution for an untreated hybrid etch sample for time delays of 0.5 to 9.5 $\mu$s (5 $\mu$s gate). The histograms display the cycle of convergence for the red shifting "green" and blue shifting "orange-red" emission features. However, the appearance of the triple peaked spectrum ($\tau_{delay}$~3.5 $\mu$s) and the time delay corresponding to the merging of the shorter wavelength and orange-red emission features to a dominant 630 nm (peak) feature, ~11.5 $\mu$s, occur on a considerably shorter time scale. The spectral intensity of the DODCI treated sample begins to drop off rapidly for time delays longer than 17.5 $\mu$s, converging to a final peak wavelength for the dominant feature at 650 nm.

A further histogram for a Rhodamine 700 treated hybrid etched sample suggests that even a 45 minute exposure has only a small effect. In fact, the convergence of the spectral features to a dominant single peak appears to occur even more rapidly than the untreated sample over the range of delay times 3.5 $\mu$s or less. A significant drop off in spectral intensity is observed to occur for time delays longer than 7.5 $\mu$s.

3. Metallization of PS Substrates

An existing challenge in fabricating PS devices rests with establishing electrical contact to the PS substrates. An exemplary embodiment of the present invention uses the methods of enhancement and stabilization of the PS substrates and the excited state fluorophors that can be created on the PS surface to enhance reduction (metallization) at the PS substrate surface. Embodiments of the present invention include using the excited state fluorophors, whose interaction and reducing capabilities are greatly enhanced relative to that of their ground states, to induce the deposition of the metal from a metal-containing solution onto the surface of the PS substrates. Metal ions can be reduced and deposited on the PS substrates and within the pores of the PS substrates. The deposition occurs in regions of the PS substrates that are illuminated with light from a light source (e.g. Xenon arc lamp, HeNe laser etc.). The illumination produces PL from the PS substrates which in turn causes metallization of the PS substrates. The thickness of the deposit upon the PS substrates is proportional to the time and intensity of exposure to the light source. While conventional electroless metal plating generally requires surface coating with Pd metal to catalyze the deposition process, exemplary embodiments of the present invention require no catalyst to deposit the metals of interest as the illuminated PS surface is itself catalyzing the deposition. These embodiments are therefore under non-catalytic conditions since no additional catalyst is needed to metallize the PS substrates.

More specifically, the post-etch method of electroless metallization of PS substrates includes treating the PS substrates with an HCl ($H_2O$) solution. The PS substrates has a microporous framework on which is superimposed a nanoporous layer. The HCl ($H_2O$) solution is at least 0.2M. In an exemplary embodiment, the HCl ($H_2O$) solution includes an alcohol. The alcohols that may be used include, but are not limited to, ethanol, methanol, other appropriate alcohols for treating PS substrates, and any combination thereof. In another exemplary embodiment, the PS substrate is treated with an HCl ($H_2O$) and alcohol solution. The next step, for both of the previous embodiments, includes treating the PS substrate with a hydrazine solution, which can remove fluorides from the porous silicon substrate. Thereafter, the PS substrate is introduced to a metal-containing solution. The metal-containing solution includes, but is not limited to, copper, silver, gold, and other appropriate electroless metals, and combinations thereof. Thereafter, the PS substrate is illuminated with a light source of less than about 750 nanometers. The light source includes, but is not limited to, a Xenon arc lamp, HeNe laser, or any other appropriate light source producing light of wavelength less than 750 nanometers for the metallization process. The illumination of the PS substrates causes the metal of the metal-containing solution to be reduced upon the surface and in the micropores and nanopores of the PS substrates. The PS substrate can also include a pattern or mask such that only portions of the PS substrate surface is metallized. The metallized PS substrate fabricated is capable of having resistances in the range of 20–1000 ohms. In addition, the metallized PS substrate can have a resistance in the range of 20–500 ohms. A preferred embodiment includes a metallized PS substrate that has a resistance in the range of 20–60 ohms.

EXAMPLE 3

Preparation of Metallized PS Samples

The following is a non-limiting illustrative example of an embodiment of the present invention which is discussed in more detail in Gole, et al., J. Electro. Soc., 147, 3785 (2000), which is herein incorporated by reference. This example is not intended to limit the scope of any embodiment of the present invention, but rather is intended to provide specific experimental conditions and results. Therefore, one skilled in the art would understand that many experimental conditions can be modified, but it is intended that these modifications are within the scope of the embodiments of this invention.

a. Preparation of PS Sample

As discussed for example 1, single crystal <100> boron doped silicon wafers with resistivities of about 50–100 ohm-cm were used in the current study. Both highly branched nanoporous and hybrid nanoporous covered microporous PS substrate samples were fabricated in an electrochemical cell constructed from high-density polyethylene. The working electrode was attached to the back of a p-type silicon wafer <100> (aluminum coated) and the counter electrode corresponded to a platinum foil placed in solution. The cell was sealed to the front of the wafer, using a clamp, as about a 1 $cm^2$ section of the wafer made contact with the solution. A magnetic stir-bar was used to prevent the build-up of hydrogen at the surface of the silicon. The electrochemical etching current was supplied by an Potentiostat/Galvanostat. The nanoporous samples were etched in an aqueous 25% HF in methanol solution while the hybrid samples were etched in a solution of 1 M $H_2O$, 1M HF, and 0.1M tetrabutylammonium percholate (TBAP), all in acetonitrile. The aqueous etched samples were etched at a current density ranging from about 2 to 30 mA/$cm^2$ and preferably about 8 mA/$cm^2$ for about 50 to 75 minutes while the hybrid samples were etched with a current density of about 6 mA/$cm^2$ for between 50 and 75 min. Using this latter procedure, pores approximately 1 to 2 $\mu$m wide by about 10 $\mu$m deep were formed, and well covered by a coating of nanoporous silicon.

Further, as discussed in example 1, single-crystal <100>, boron-doped silicon wafers (substrate) of resistivity ranging from about 1 to about 50 ohm/cm² were also etched in an aqueous HF solution. For several of the experiments (about 20% concentration of HF in methanol), a 300-nm thin film of aluminum was sputtered onto the backside of the wafers. Electrical connections were made to the wafers by connecting a wire to the thin film of aluminum using conductive paint. The wire and aluminum film were then covered with a layer of black wax, leaving only the front surface of the silicon exposed to the etching solution. Both the wired silicon-wafer as one electrode and a platinum wire as a counter-electrode could be connected through a Teflon cap, which was tightly fitted to a cuvette containing the etch solution. Ohmic contacts were made to the wafer by connecting a wire to the thin film of aluminum using conductive paint. Etching currents ranged from about 2 to 30 mA/cm², but the samples considered here were usually etched at 8 mA/cm² for 10 minutes.

After the nanoporous and hybrid etches were complete, the samples were removed to air, washed with methanol, and dried. For the majority of the samples, the etched PS substrate samples were treated with anhydrous concentrated hydrazine (about 30 M) to remove fluorine from the surface via a reaction which converts the fluorine and hydrazine to nitrogen and HF.

b. PL Stabilization Using HCl

Several of the samples were later treated with a 6M HCl/MeOH solution to: (1) enhance the photoluminescence and (2) stabilize the photoluminescence quantum yield.

c. Preparation of the Electroless Plating Solution

An electroless copper solution was prepared, following standard procedures known in the art, from $CuSO_4 \cdot 5H_2O$ (0.76 g), sodium potassium tartrate (4.92 g), formaldehyde (2 ml), and NaOH (0.80 g) diluted to 200 ml in doubly de-ionized water. A slightly modified procedure was used to prepare an electroless silver solution. First 0.75 M $NH_4NO_3$ (12 g/200 ml) and 2 M $NH_3$ (24.3 mL $NH_4OH$/ZOO ml $H_2O$) solutions were mixed together and diluted in a 100 mL volumetric flask with doubly ionized water. To this solution was added 0.09 M $AgNO_3$ (1.36 g $AgNO_3$/200 ml) followed by 0.1 M $Co(NO_3)_2 \cdot 6H_2O$ (5.82 g diluted into 50 ml of doubly de-ionized water). To this mixture was added sufficient doubly de-ionized water to bring the total solution volume to 200 ml. The copper and silver solutions were maintained in a refrigerator at 20° C. until they were used. As discussed above, other metal-containing solutions can be produced and used.

d. Metallization

Both the nanoporous and hybrid macroporous-nanoporous PS samples were exposed to the copper and silver electroless solutions either directly or after the samples were treated with HCl. The majority of the samples were also treated with anhydrous hydrazine. Samples were exposed directly to the electroless solutions both under ultraviolet/visible (UV/Vis) and HeNe laser photoluminescence excitation (PLE), in complete darkness, or in the presence of laboratory room lights. The observation of the reduction of the electroless solution metallic ions and the subsequent metal deposition was found to be surface illumination dependent.

The nature of the contact formation to the PS surface formed from <100> p-type silicon is now discussed. To place electroless metal contacts on the PS surface, this surface was first passivated with a non-stoichiometric silicon nitride, $SiN_x$, layer which was grown by plasma enhanced chemical vapor deposition, PECVD. The openings in the $SiN_x$ layer needed for formation of the porous layer were made by reactive ion etching, RIE. After an anodic etch, the porous layer was prepared and electroless copper (Cu) or silver (Ag) was deposited on the surface of this PS substrate layer to form the metal contacts necessary to make a resistance measurement.

Data was obtained for PS substrate samples exposed to electroless Ag and Cu solutions at about 16 and 30° C. For the vast majority of these experiments the samples were bathed in anhydrous hydrazine for periods of 30, 60, or 90 minutes before exposure in the electroless solutions. This treatment was carried out to remove fluorine based constituents from the PS substrate surface. With the removal of fluorine, the effects of optical pumping as it produces a long-lived photoluminescent emitter, can be readily evaluated. PS substrate samples, which are photoluminescent, are capable of plating silver and copper from an electroless solution, in which they are in contact, if exposed to UV/visible light or when exposed to a HeNe laser. If the PS surface is not photoluminescent or the PL from a photoluminescent surface is quenched, the deposition of copper or silver is diminished or completely absent. While temperature is an important consideration in these experiments, measurements of the very small surface temperature change as a function of exposure to the light sources used in this study demonstrate that the metal plating is not the result of a surface heating effect. However, an increased ambient temperature for the PS substrate surface, especially for those experiments involving electroless silver plating, can lead to an enhancement of the deposition process. In other words, the plating is more pronounced and more difficult to control precisely at 30° C. than at 16° C.

Photoluminescent PS substrate samples were clamped to the surface of a hollow copper block whose temperature could be adjusted by flowing water through a slush bath configuration at room or ice temperatures. Simultaneously, the sample under study was placed under a ring used to hold the electroless solution as the entire experiment was carried out under a flowing stream of high purity argon. Over the course of an experiment, the surface temperature was measured with a thermocouple. While this system could be operated at temperatures considerably lower than the ice bath temperature, $T_{surface}$(measured)=16±1° C., it was found that: (1) this was unnecessary to control the electroless process; and (2) that colder device temperatures eventually led to the undesirable condensation of the electroless solution. The temperature rise associated or induced by the high intensity UV/visible lamp, never exceeded 1.5° C. No temperature rise was recorded for those experiments with the HeNe laser (even if the laser was focused onto the tip of the thermocouple).

The reduction of silver from the electroless solution was found to be considerably more efficient than was that of copper from its electroless solution. For the silver samples at 16° C., hydrazine exposure was systematically varied from 30 to 60 to 90 seconds demonstrating only a moderate effect with increased exposure on the observed plating. Samples treated with hydrazine plate at a much slower rate than do untreated samples which have maintained a fluoride constituency on the PS substrate surface. Results were obtained for both aqueous etched and hybrid etched samples, the latter interacting with the electroless solutions notably more effectively.

SEM micrographs of copper and silver deposition into the pores of a hybrid macroporous/nanoporous sample at 16° C. demonstrate the deposition of metal to the walls of the micropores. The results of the resistance measurements on the initially generated electroless copper connections indicate resistances ranging from about 20 ohms to about 1000 ohms.

The electroless copper solution used in these experiments is considerably more stable (kinetically) than the electroless silver solution. In contrast to a freshly formed PS substrate surface, there is no plating on a c-Si substrate from the electroless copper solution and likewise there is no plating on PS substrate samples which have been oxidized in air for periods exceeding several weeks. As a freshly formed photoluminescent sample readily plates copper at room temperature, the plating ability of a PS substrate sample which has been subjected to extended oxidation can be restored with a brief exposure to a HCl solution. Samples which are exposed to the electroless copper bath will generally not plate copper if they: (1) are placed in a darkened location; (2) are soaked in etching solution in the absence of current flow before exposure; (3) are a heated at their surface in the presence of the electroless bath; or (4) have undergone a previous PL quenching process.

Thus, the plating process appears to require, at least in part, that a treated PS substrate surface be photoluminescent. However, it is known in the art that copper can be reductively deposited, in small concentration, on a PS substrate surface from an aqueous $Cu^{+2}$ solution in the absence of photoexcitation. Thus, anhydrous hydrazine has been introduced to modify the initially prepared PS substrate as a means of removing the fluoride centers on the surface, which may act as reducing centers for $Cu^{+2}$ (aq) ions. Upon treatment with hydrazine the copper reduction at the PS substrate surface (1) is slowed to an extent which allows a significant improvement in the degree of control of the metallization process, (2) clearly becomes a function of surface excited state fluorophors, and (3) is notably more amenable to pattern formation. The exposure of an untreated PS substrate surface, with its surface fluoride constituency, to the HeNe laser produces a photodefineable pattern in 5 minutes whereas the pattern produced with a Xe ArC lamp, with a plating time approaching one minute, is not photodefineable. Surface fluoride, like palladium, appears to act as a catalyst for the reduction process.

The PS substrates, whose luminescence has been quenched, cannot be patterned by the present method. While the mechanism of electroless deposition onto PS might result in part from electron-hole pair generation within the PS substrates it more likely results from excited state electron transfer involving surface-confined silicon oxyhydrides.

4. PS Sensors

The following is a non-limiting illustrative example of an embodiment of the present invention. For more information relating to embodiments of the present invention, see Seals, et al., J. Applied Physics, 91, 2519 (2000) and Gole, et al., J. Electrochem. Soc., 147, 3785 (2000), which are herein incorporated by reference. This example is not intended to limit the scope of any embodiment of the present invention, but rather is intended to provide specific experimental conditions and results. Therefore, one skilled in the art would understand that many experimental conditions can be modified, but it is intended that these modifications are within the scope of the embodiments of this invention.

Embodiments of the present invention provide for a PS sensor. The PS sensor includes a silicon substrate, a PS layer on a portion of the silicon substrate, and a front contact disposed onto a portion of the PS region. The PS region can include a nanoporous or a macroporous and nanoporous hybrid framework. In the preferred embodiment, the front contact can be disposed within the macroporous and nanoporous hybrid framework as well as extend above the PS region. The front contact can include one or more front contact portions made of metals such as, for example, copper, silver, and gold.

The PS sensors can be used to detect gases or liquids. The PS sensors have a contact resistance between the front contact and the PS between about 10 and 100 ohms, 20 to 100 ohms, and preferably about 20 and 60 ohms. In addition, the PS sensors have a resistivity between about 0.01 ohm/$cm^2$ to 1 ohm/$cm^2$, and preferably about 0.1 ohm/$cm^2$ to 1 ohm/$cm^2$, where the resistivity includes the PS region. The PS sensors operate at a bias voltage of between about 1 and 20 millivolts, and preferably about 1 to 10 millivolts. In addition, the PS sensors have a sensitivity of between about 10 and 100 parts per million (ppm). However, the sensitivity may be lower since it is difficult to acquire an independently verified sample below 10 ppm. The contact resistance, the resistivity, the operating bias voltage, and the sensitivity of the PS sensors should be contrasted to other gas sensors that have a spreading resistance of about 200 kiloohms to 1 megaohm, have operating voltages between about 2 to 5 volts, and have a sensitivity between about 100 and 1000 ppm.

The PS sensor can be used in a variety of ways including, but not limited to, a stand-alone detector, an array of stand-alone detectors, a detector for gas chromatography (e.g., miniature gas chromatography), a detector for liquid chromatography, or a biosensor. Gas chromatographs, liquid chromatographs, and biosensors are well known in the art. The PS sensor can be used to detect gases (e.g., combustion generated gases such as carbon monoxide, carbon dioxide, sulfur dioxides, nitrogen oxides, hydrogen sulfide, and hydrogen cyanide) and liquids (e.g., organic, inorganic, and biological based liquid). In particular, PS gas sensors, in accordance with the present invention, can have a rapid and reversible response to analyte gases (e.g., hydrochloric acid, ammonia, and nitric oxide) at room temperature.

In some embodiments, the PS sensor can be used in conjunction with a selective film (e.g., metal, metal oxide, metalloid, metalloid oxide, non-metal, or biomolecular film) or a thin film of a catalytic material incorporated into the PS macroporous/nanoporous structure. For example, the PS layer of the PS sensor can be coated with a thin layer of metal such that the metal penetrates within the PS macroporous/nanoporous structure. The metals can include, but are not limited to, palladium (Pd), iridium (Ir), rhodium (Rh), vanadium (Va), and ruthenium (Ru). In this regard, the PS sensor can be designed to provide selectivity for a particular gas/liquid.

In another example, a nanostructure (e.g., a nanosphere, a nanowire, a nanodisk, and a nanobelt) and/or a coated nanostructure (i.e., a nanostructure having a material (e.g., a metal, a metal oxide, metalloid, or metalloid oxide) disposed on the nanostructure can be incorporated into the macroporous/nanoporous framework of the PS layer. For example, the nanostructure can be made of materials such as, but not limited to, oxide, silicon (Si), tin (Sn), chromium (Cr), iron (Fe), nickel (Ni), silver (Ag), titanium (Ti), cobalt (Co), zinc (Zn), platinum (Pt), palladium (Pd), osmium (Os), gold (Au), lead (Pb), iridium (Ir), molybdenum (Mo), vanadium (V), aluminum (Al), silicon oxide ($SiO_x$), tin dioxide ($SnO_2$), chromia ($Cr_2O_3$), iron oxide ($Fe_2O_3$, $Fe_3O_4$, or FeO), nickel oxide (NiO), silver oxide (AgO), titanium oxide ($TiO_2$), cobalt oxide ($Co_2O_3$, $Co_3O_4$, or CoO), zinc oxide (ZnO), platinum oxide (PtO), palladium oxide (PdO), vanadium oxide ($VO_2$), molybdenum oxide ($MoO_2$), lead oxide (PbO), titanium oxide ($TiO_x$), titanium nitride ($TiN_x$), titanium oxinitride ($TiO_xN_y$), and combinations thereof. In this regard, the PS sensor can be designed to provide selectivity for a particular gas/liquid.

In still another embodiment, a portion of the PS region 19 can be coated with a thin film of a biomolecule to enhance the selectivity of the PS sensor towards a particular gas or liquid (e.g., glusose). For example, the PS region 19 can be coated with a thin layer of a biomolecule such as, for example, an antibody, a polypeptide, or a polynucleotide.

In addition, an array of PS sensors can be used to enhance sensing selectivity as the array of PS sensors provide multiple data points per tested sample and can be modified to provide selectivity for one gas/liquid over another in various regions of the PS sensor array. Thus, the array of PS sensors can include PS sensors sensitive to select gases and/or liquids. In this regard, the array of PS sensors can detect multiple analytes simultaneously, while also enhancing sensing selectivity.

Figure 1B:
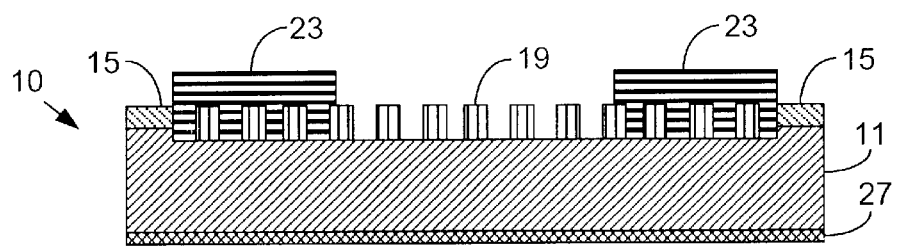
FIG. 1B is a cross-sectional view of the porous silicon sensor shown in FIG. 1A in the A—A direction.

FIG. 1A illustrates a top view of a PS sensor 10, while FIG. 1B illustrates a cross-sectional view of the PS sensor 10 in the A—A direction shown in FIG. 1A. The PS sensor 10 shown in FIGS. 1A and 1B includes a silicon substrate 11, a $SiN_x$ layer 15, a PS layer 19, and a front contact 23. In addition, the PS sensor 10 can include a backside contact 27, however this is optional.

The $SiN_x$ layer 15 is disposed on the silicon substrate 11. The PS layer 19 is fabricated from the silicon substrate 11 using techniques discussed above to form a nanoporous (not depicted in FIGS. 1A and 1B) or a macroporous/nanoporous PS framework. As depicted in FIG. 1B, a portion of the front contact 23 is disposed in the PS layer 19, while the remaining portion of the front contact 23 extends above the PS layer 19. In other words, the front contact 23 is included within the macroporous/nanoporous regions of the PS layer 19, which achieves a lower contact resistance between the front contact 23 and the PS layer 19. Alternatively, the front contact 23 can be disposed on top of the PS layer 19.

The silicon substrate 111 can include wafers, such as, but not limited to, silicon wafers, doped silicon wafers, p-type silicon wafers, and boron doped silicon wafers. The silicon substrate 11 can have dimensions appropriate to form a PS region as well as appropriate for a particular application. The $SiN_x$ layer 15 can be deposited using PECVD (plasma enhanced chemical vapor deposition) at about 200° C. to 300° C., and preferably at 250° C. in a Plasma Therm™ (St. Petersburgh, Fla.). The $SiN_x$ layer can be between about 100 to 300 nanometers (nm) thick, and preferably 200 nm thick. Other materials can be used in place of the $SiN_x$ layer 15 such as, but not limited to, a polymer layer, a $SiO_xN_y$ layer, an insulating dielectric film, a ceramic layer, photoresist layer, and polyimide layer.

The PS region 19 can include a nanoporous region, or preferably a macroporous/nanoporous framework (i.e., a macroporous framework on which is superimposed a nanoporous layer). The macroporous framework can include pores approximately 1 to 2 $\mu$m wide and about 10 $\mu$m deep, while also having nanopores throughout the macroporous framework. The PS region 19 can be prepared by electrochemically etching a portion of the silicon substrate with acetonitrile, hydrogen fluoride, and TBAP, for example. The photoluminescence (PL) of the PS region can be enhanced and stabilized by treating the PS region 19 with a solution that can include components such as, but not limited to, an aqueous hydrochloric and aqueous hydrochloric acid/alcohol solution. Additional details regarding the preparation of the PS region 19, and enhancement and stabilization of the PL of the PS region 19 are presented in more detail above.

As described above, the front contact 23 can be disposed within the PS region 19. In general, the front contact is formed by exposing the PS region 19 to a metal-containing solution and illuminating portions of the PS region 19 with an appropriate light source, as discussed above. The illumination causes PL of selected portions of the PS region 19, which causes the metal to metallize to the selected portions of the PS region 19. Additional details regarding metallization are described above.

The front contact 23 includes two contacts (as shown in FIGS. 1A and 1B). However, the front contact 23 can include one or more contacts (i.e., four contacts). In addition, the configuration of the front contact 23 can include additional configurations to the two shown in FIGS. 1A and 1B, and 2A and 2B. The front contact 23 can be made of metals, such as, but not limited to, gold (Au), silver (Ag), and copper (Cu). In addition, the front contact 23 can be made of conductive metal oxides such as, but not limited to, indium tin oxide ($InSnO_2$) and ruthenium oxide ($RuO_2$).

The backside contact 27 can be made of metal, such as, but not limited to, aluminum (Al), copper (Cu), tungsten (W), chromium (Cr), gallium (Ga), and gold (Au). In addition, the front contact 23 can be made of conductive metal oxides such as, but not limited to, indium tin oxide ($InSnO_2$) and ruthenium oxide ($RuO_2$). The backside contact 27 is used to apply a direct current bias to the backside of the silicon substrate 11.

Figure 2A:
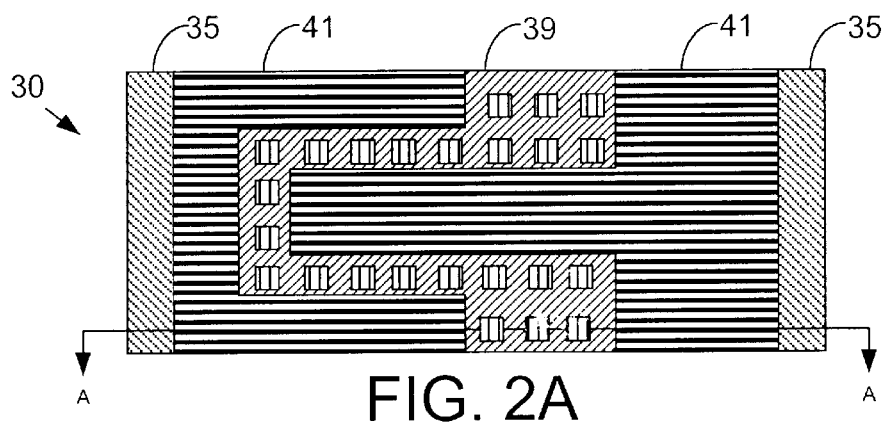
Figure 2B:
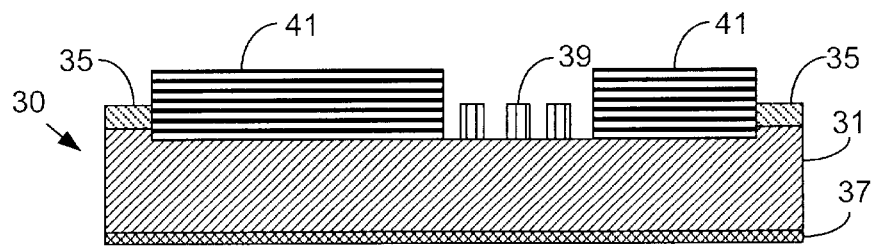
FIG. 2B is a cross-sectional view of the porous silicon sensor shown in FIG. 2A in the A—A direction.

FIG. 2A illustrates a top view of a PS gas sensor 30, while FIG. 2B illustrates a cross-sectional view of the PS gas sensor 30 in the A—A direction shown in FIG. 2A. The PS gas sensor 30 shown includes a silicon substrate 31, a $SiN_x$ layer 35, a PS layer 39, and a front contact 41. FIGS. 2A and 2B illustrate a different contact configuration. As indicated above, it is contemplated that additional contact configurations are possible and thus are included within the scope of this document. In addition, the PS gas sensor 30 can include a backside contact 37, however this is optional.

For the purposes of illustration only, and without limitation, embodiments of the present invention will be described with particular reference to the below-described fabrication method. Note that not every step in the process is described with reference to the process described in the figures hereinafter. Therefore, the following fabrication process is not intended to be an exhaustive list that includes every step required for the fabrication the embodiments of the PS sensor 10.

Figure 3A:
FIGS. 3A through 3K are cross-sectional views of a representative fabrication of the porous silicon sensor shown in FIGS. 1A and 1B.
Figure 3B:
Figure 3C:
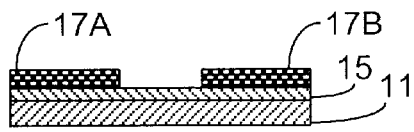

FIGS. 3A–3K illustrate cross-section views of the PS sensor 10 shown in FIG. 1B during a representative fabrication process. FIG. 3A illustrates a silicon substrate 11 having an $SiN_x$ layer 15 disposed thereon. FIG. 3B illustrates a mask 17 disposed onto the $SiN_x$ layer 15, while FIG. 3C illustrates the patterning of the mask 17 into two mask regions 17A and 17B. The mask 17 can be made of materials such as, but not limited to, metals.

Figure 3D:
Figure 3E:
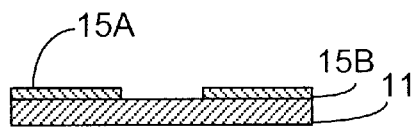

FIG. 3D illustrates the etching of the $SiN_x$ region 15 into two $SiN_x$ regions 15A and 15B using reactive ion etching. FIG. 3E illustrates the removal of the two mask regions 17A and 17B thereby exposing the two $SiN_x$ regions 15A and 15B.

Figure 3F:
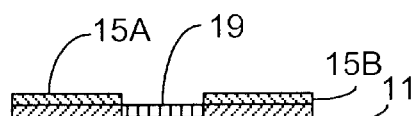

FIG. 3F illustrates the silicon substrate 11 after a portion of the silicon substrate 11 is electrochemically etched to form a PS region 19 disposed between the two $SiN_x$ regions 15A and 15B.

Figure 3G:
Figure 3H:
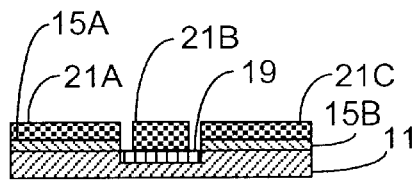

FIG. 3G illustrates a mask 21 disposed onto the two $SiN_x$ regions 15A and 15B and the PS region 19, while FIG. 3H illustrates the patterning of the mask 21 into three mask regions 21A, 21B, and 21C. The pattern of the mask regions 21A, 21B, and 21C exposes two portions of the PS region 19.

Figure 3I:
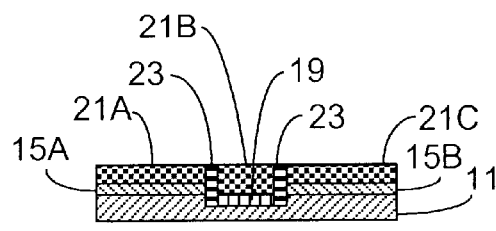

FIG. 3I illustrates the front contact 23 disposed onto the two portions of the PS region 19. The front contact 23 is disposed using the PL of the two PS regions 19 after the two PS regions 19 are illuminated with an appropriate light source, as discussed above. The front contact 23 can be disposed within the macroporous/nanoporous regions of the two PS regions 19. Alternatively, the front contact 23 can be disposed onto the two portions of the PS substrate 19 via techniques such as, but not limited to, electron-beam evaporation, sputtering, silk-screen printing, and electroplating.

Figure 3J:
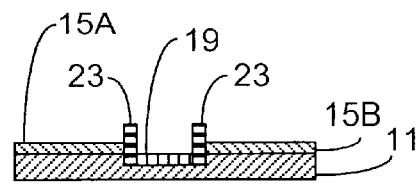
Figure 3K:
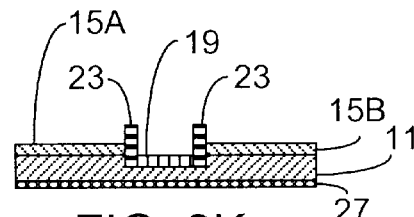

FIG. 3J illustrates the removal of the three mask regions 21A, 21B, and 21C, thereby exposing the front contact 23. FIG. 3K illustrates the backside contact 27 disposed onto the backside of the silicon substrate 11 using techniques such as, but not limited to, electron-beam evaporation, sputtering, silk-screen printing, and electroplating.

EXAMPLE 4 a. Preparation and Evaluation of a PS Sensor

The following is an illustrative example of an embodiment of a PS gas sensor in accordance with the present invention. Initially, cleaned (100) silicon wafers, [p-type, 2–20 ohm-cm, 2 inch diameter (available from Wafer World)] were covered with a 200 nm thick film of PECVD $SiN_x$ deposited at 250° C. in a Plasma Therm. The film thickness was measured with an ellipsometer and the index of refraction was found to be about 1.8 at a wavelength of about 600 nanometers. A standard Shipley AZ 1827 positive photoresist process was used to pattern the $SiN_x$, which was subsequently removed by reactive ion etching in $CHF_3$ in the Plasma Therm™ (etch rate about 36 nanometers per minute). The exposed regions serve as the sites utilized for the PS region formation via electrochemical etching in a solution of 1M acetonitrile, 1M HF, and 0.1M TBAP, as described above.

The PS region formed has a hybrid structure that includes macropores impregnated by a nanoporous overcoat. Having formed a PS region, a second photolithography step is used for electrode definition. Electrical contacts produced by both electroless deposition (electro-less) and electron-beam evaporation (e-beam) have been found to produce a variety of resistances between about 28 ohms and 5 kilo-ohms. In the electroless process the walls for the hybrid structure of the PS region can be coated with a thin submicron film of the metals such as, for example, copper (Cu), silver (Ag), or gold (Au), which are reduced from the electroless solution, as described above. After contact formation, the resist is removed with acetone.

To facilitate bias measurements, an ohmic backside contact was applied to the backside of the silicon substrate. A 100 nanometer aluminum film was deposited by screen printing aluminum paste and rapid thermal annealing in an RP-10 (available from RPI systems, Inc.) for about 5 minutes at 850° C. Alloying leads to the formation a p+ layer of the silicon substrate in contact with the aluminum provides a low contact resistance between the aluminum metal and the silicon substrate. The high temperature alloying step does not appear to have any adverse effect on the PS layer. Thereafter, the modified silicon substrate was stored in dry nitrogen prior to packaging and wire bonding.

Thereafter, the PS gas sensor was mounted onto a 12 pin flat pack (available from OLIN AEGIS Inc.) and wire bonded with 1.5 mil gold wire to the contact pads. Silver epoxy (Ablebond 84-1 LM that is available from Abelstick Company) was placed on the pad to strengthen the connection, which are at cured at room temperature.

b. Sensor Evaluation

The PS gas sensor was evaluated using an experimental setup that includes a small, ⅛th inch ID Tygon tubing sheathed onto ⅛th inch OD stainless steel tubing. The steel tubing was connected to a 150 millimeter Shield Industrial Flow meter (Air products, Inc.) and a stainless steel chamber, to which the PS gas sensor was mounted, with an internal volume approximately 1 $cm^3$. The PS gas sensor was electrically connected to a Solartron impedance analyzer (SI 1260, Solartron Mobrey, Houston, Tex.) and the impedance analyzer was connected to a PC computer for data acquisition running Z-view (Scribner Associates, Inc.). Open and short circuit calibrations were stored in the instrument to correct for cable impedance. The impedance of the PS gas sensor was measured over a frequency range 100 Hz to 20 KHz with an integration time of 1 second. The impedance was found to be frequency independent. The time response was measured at a fixed frequency of 1 kHz, generally with a 10 millivolt RMS drive voltage at room temperature.

A flow of nitrogen gas, controlled to a rate less than 1 sccm, was introduced to the reaction chamber. After the nitrogen flow was stopped, the test gas was introduced into the measurement cell. Gases tested included 100 ppm of HCl, $NH_3$, and NO in argon that were independently calibrated (Air Products). After approximately 30 seconds a pump was turned on to evacuate the measurement cell. Impedance readings were recorded to data files in a computer automatically.

Figure 4A:
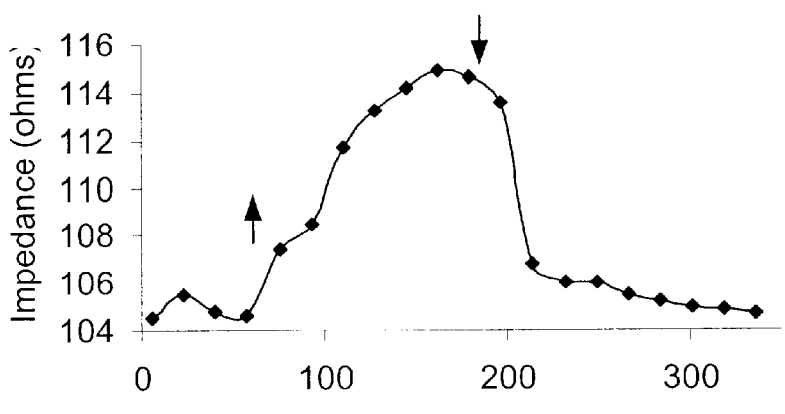
FIGS. 4A 4B, and 4C are graphs plotting the response of a porous silicon sensor in response to exposure to hydrochloric acid, ammonia, and nitric oxide, respectively. The up arrow indicates the point at which the gas was introduced to the porous silicon sensor in a chamber, while the down arrow indicates the point at which the gas was evacuated from the chamber.
Figure 4B:
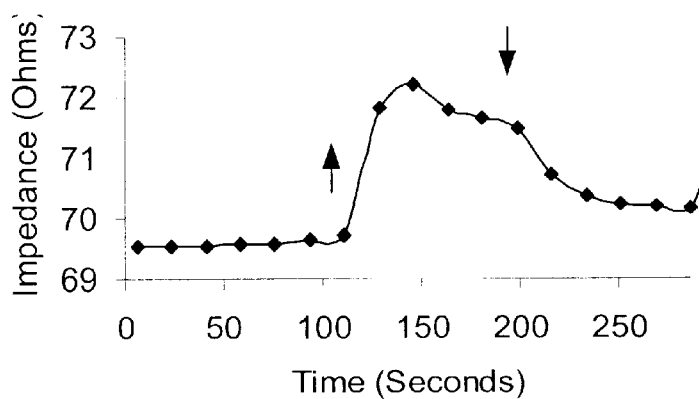
Figure 4C:
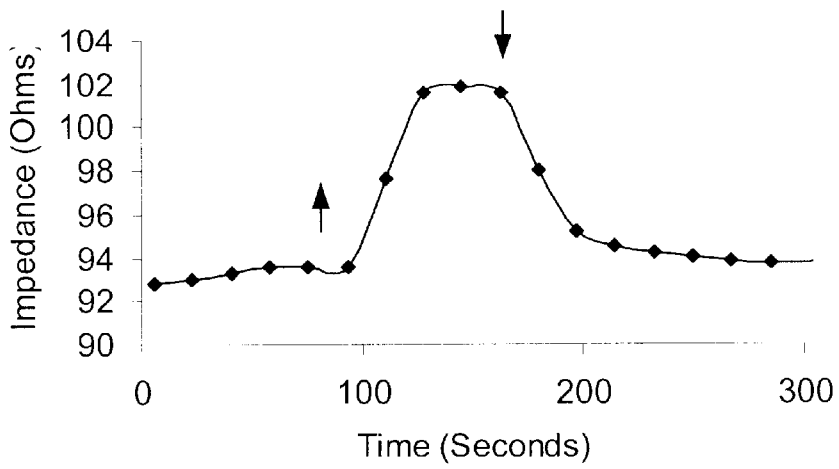

FIGS. 4A through 4C depict the response of the interdigitated PS gas sensor to concentrations of 100 ppm of HCl, $NH_3$, and NO corresponding to a change of impedance of 8, 2.5, and 12 ohms respectively. The up arrow indicates the point at which the gas was introduced to the PS sensor in a reaction cell, while the down arrow indicates the point at which the gas was evacuated from the reaction cell. A rapid return of the impedance to its baseline impedance value occurred when the reaction cell was evacuated. Although, the absolute value of the impedance has changed somewhat due to some baseline drift, this is corrected for by determining the impedance prior to the experiment. Also note that the data presented in FIGS. 4A through 4C are taken for the highest resistance contacts employed in this study.

c. Discussion

The PS gas sensors in accordance with the present invention show a rapid and reversible response to the analyte gases at room temperature. Compared to the limited reports of conductimetric PS gas sensors, the response is more sensitive, allowing the detection of HCl and ammonia and at a reduced applied DC bias. A rapid response suggests a surface reaction that is easily reversed. The response times indicate a time constant for all analytes on the order of 1 minute, however, this was strongly affected by the flow characteristics of the measurement system. In particular, the flow cell internal volume (1 $cm^3$) and flow rate of 1 sccm. Hence, the response time of the PS gas sensor itself may indeed be more rapid.

Absorption of molecules onto the porous silicon layer can be due to van-der Waals interactions, dipole-dipole interactions and/or electron exchange with surface states. The extent to which each is responsible in this case has yet to be determined. The magnitude of the response is a function of the analyte concentration (data not shown) indicating, for example, a larger impedance change at higher ammonia concentrations up to 1% ammonia in argon. For HCl, $NH_3$, and NO the magnitude of the response is not in agreement with the relative dipole moments of these gas molecules. This data suggests that a form of electron exchange, similar to that for the conductive metal oxides contributes to the channel conductivity modulation The PS gas sensor of the present invention is to be distinguished from those based on optical means of interrogation that have been or are currently being developed to make use of the PS photoluminescence employing (1) PL quenching, (2) laser interferometry, or (3) microcavity designs. The latter two approaches also represent more complex designs subject to more stringent fabrication and/or application procedures than the PS sensor discussed here.

Work on the electrical properties of PS has indicated that the film has a reduced number of carriers available for conduction. Also, some experiments suggest that Au/PS junctions might exhibit barrier heights of the order of 0.74 eV. While a barrier height can be sensitive to absorbed species, it appears that the low resistance of the PS gas sensors indicates a film based mechanism rather than barrier height modulation. The ohmic behavior of the contacts also supports this model; however, temperature dependent measurements of the junction electrical characteristics could be used to provide additional evidence.

The sensitivity of the PS sensor defined as the normalized resistance change per ppm of analyte concentration can be compared to other metal oxide sensors. For $NH_3$ and NO the sensitivity was 0.1%/ppm and for HCl 0.03%/ppm. This sensitivity is not as high as microfabricated $SnO_2$ sensors, which are typically 1%/ppm for reducing gases. However, the detection limits for $NH_3$ and NO depend upon the nano-structural properties of the $SnO_2$ and the manner in which it is prepared. Similar detection limits are possible for amperometric sensors like NASICON 28 with levels in the 0.1 ppm range. However, the sensitivities and response times of the PS gas sensor in accordance with the present invention are quite reasonable for a sensor operating at room temperature that has not been optimized for these analytes. For the data collected thus far at 100° C., the response of the PS gas sensor is notably more rapid. Further, the sensors operation at considerably higher partial pressures of HCl, $NH_3$, and NO extending to 1000 and 10,000 ppm is not compromised.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A sensor, comprising:
   a silicon substrate having a porous silicon region, wherein a front contact is disposed on a portion of the porous silicon region, wherein the contact resistance between the porous silicon region and the front contact is between about 10 ohms and 100 ohms, and wherein the resistivity is between about 0.01 ohm/centimeter squared ($cm^2$) and 1 ohm/$cm^2$.

2. The sensor of claim 1, further comprising a back contact attached to a backside of the silicon substrate.

3. The sensor of claim 2, wherein the back contact comprises a metal selected from aluminum, nickel, and gold.

4. The sensor of claim 1, wherein the front contact comprises a metal selected from gold, silver, and copper.

5. The sensor of claim 1, wherein the contact resistance is between about 20 ohms and 60 ohms.

6. The sensor of claim 1, wherein the sensor is operative to detect a gas.

7. The sensor of claim 1, wherein the sensor is operative to detect a liquid.

8. The sensor of claim 1, wherein the sensor is operative to detect a biomolecule.

9. The sensor of claim 1, wherein the sensor is operative to detect about between about 10 parts per million (ppm) to 100 ppm of hydrochloric acid at a bias of between about 1 millivolts and 10 millivolts.

10. The sensor of claim 1, wherein the sensor is operative to detect about between about 10 parts per million (ppm) to 100 ppm of ammonia at a bias of between about 1 millivolts and 10 millivolts.

11. The sensor of claim 1, wherein the sensor is operative to detect about between about 10 parts per million (ppm) to 100 ppm of nitric oxide at a bias of between about 1 millivolts and 10 millivolts.

12. The sensor of claim 1, wherein the porous silicon region includes a macroporous framework on which is superimposed a nanoporous layer.

13. The sensor of claim 12, wherein the macroporous framework includes pores approximately 1 to 2 $\mu$m wide by about 10 $\mu$m deep.

14. The sensor of claim 1, wherein the porous silicon region is coated with a metal selected from platinum, palladium, iridium, rhodium, vanadium, and ruthenium.

15. The sensor of claim 1, wherein the porous silicon region includes nanostructures disposed within the porous silicon framework.

16. A gas chromatograph, comprising:
   a detector including a gas sensor that includes a silicon substrate having a porous silicon region, wherein a front contact is disposed on a portion of the porous silicon region, and wherein the contact resistance between the porous silicon region and the front contact is between about 10 ohms and 100 ohms.

17. A liquid chromatograph, comprising:
   a detector including a gas sensor that includes a silicon substrate having a porous silicon region, wherein a front contact is disposed on a portion of the porous silicon region, and wherein the contact resistance between the porous silicon region and the front contact is between about 10 ohms and 100 ohms.

* * * * *